(12) United States Patent
Grafton et al.

(10) Patent No.: US 7,883,528 B2
(45) Date of Patent: Feb. 8, 2011

(54) FULLY THREADED SUTURE ANCHOR WITH INSERT-MOLDED SUTURE

(75) Inventors: R. Donald Grafton, Naples, FL (US); Stephen S. Burkhart, San Antonio, TX (US)

(73) Assignee: Arthrex, Inc., Naples, FL (US)

( * ) Notice: Subject to any disclaimer, the term of this patent is extended or adjusted under 35 U.S.C. 154(b) by 806 days.

(21) Appl. No.: 10/660,601

(22) Filed: Sep. 12, 2003

(65) Prior Publication Data

US 2004/0106950 A1  Jun. 3, 2004

Related U.S. Application Data

(60) Provisional application No. 60/409,929, filed on Sep. 12, 2002.

(51) Int. Cl.
*A61B 17/04* (2006.01)
(52) U.S. Cl. ...................... 606/232; 606/301
(58) Field of Classification Search ................ 606/232, 606/72, 73, 60, 222–227; 411/426, 308
See application file for complete search history.

(56) References Cited

U.S. PATENT DOCUMENTS

| | | | | |
|---|---|---|---|---|
| 74,489 | A * | 2/1868 | Bidwell | 411/386 |
| 5,417,533 | A * | 5/1995 | Lasner | 411/426 |
| 5,571,139 | A * | 11/1996 | Jenkins, Jr. | 606/232 |
| 5,584,835 | A * | 12/1996 | Greenfield | 606/232 |
| 5,695,497 | A * | 12/1997 | Stahelin | 606/73 |
| 5,964,739 | A * | 10/1999 | Champ | 604/263 |
| 5,964,783 | A * | 10/1999 | Grafton et al. | 606/232 |
| 6,214,031 | B1 * | 4/2001 | Schmieding et al. | 606/232 |
| 6,319,270 | B1 * | 11/2001 | Grafton et al. | 606/232 |
| 6,454,772 | B1 * | 9/2002 | Jackson | 606/73 |
| 6,652,563 | B2 * | 11/2003 | Dreyfuss | 606/232 |
| 6,666,877 | B2 * | 12/2003 | Morgan et al. | 606/232 |
| 7,226,469 | B2 * | 6/2007 | Benavitz et al. | 606/232 |

* cited by examiner

*Primary Examiner*—(Jackie) Tan-Uyen T Ho
*Assistant Examiner*—Melissa Ryckman
(74) *Attorney, Agent, or Firm*—Dickstein Shapiro LLP

(57) ABSTRACT

A fully threaded, bioabsorbable suture anchor with a suture loop that is disposed internally within the suture anchor. The suture loop is insert-molded into the anchor. The fully threaded design provides improved fixation, while the insert-molded internal suture loop serves as a recessed eyelet for a second (knot-tying) suture.

17 Claims, 5 Drawing Sheets

FULLY THREADED SUTURE ANCHOR WITH INSERT-MOLDED SUTURE

CROSS-REFERENCE TO RELATED APPLICATIONS

This application claims the benefit of U.S. Provisional Application Ser. No. 60/409,929, filed Sep. 12, 2002, the entire disclosure of which is incorporated by reference herein.

FIELD OF THE INVENTION

The present invention relates to an apparatus and method for anchoring surgical suture to bone. More specifically, the present invention relates to arthroscopic apparatus and methods for anchoring suture to bone using a fully-threaded bioabsorbable suture anchor having a suture loop molded directly into the suture anchor.

BACKGROUND OF THE INVENTION

When soft tissue tears away from bone, reattachment becomes necessary. Various devices, including sutures alone, screws, staples, wedges, and plugs have been used in the prior art to secure soft tissue to bone.

Recently, various types of threaded suture anchors have been developed for this purpose. Some threaded suture anchors are designed to be inserted into a pre-drilled hole. Other suture anchors are self-tapping.

U.S. Pat. No. 5,964,783 to Grafton et al., the disclosure of which is incorporated by reference herein, discloses a threaded bioabsorbable suture anchor provided with a loop of suture that is insert-molded directly into the suture anchor during manufacturing. The proximal end of the suture anchor body of the '783 patent is provided with a non-threaded hexagonal drive head. The insert-molded suture preferably extends through the entire length of the suture anchor body and exits through the drive head at the proximal end of the anchor to form a loop of suture external to the suture anchor. In this manner, the suture forming the loop is secured effectively to the threaded suture anchor and is prevented from becoming detached from the anchor. However, because the suture anchor of '783 patent is provided with the non-threaded hexagonal head, the threads of the threaded anchor body do not reach the top of the cortical bone when the suture anchor is installed. Thus, the threaded anchor body tends to move up to the bone surface by at least a distance equal to the length of the non-threaded hexagonal head, such that the drive head may become proud to the surface. Moreover, the suture of the eyelet, which is disposed outside the suture anchor in back of the drive head, may abrade the adjacent tissue.

Accordingly, a need exists for an improved threaded bioabsorbable suture anchor which is threaded along the entire length of the anchor body, including the drive head, to improve fixation of the anchor in bone. In addition, a need exists for a bioabsorbable suture anchor having a suture loop that does not extend beyond the drive head and does not abrade tissue.

SUMMARY OF THE INVENTION

The suture anchor of the present invention overcomes disadvantages of the prior art, such as those noted above, by providing a fully-threaded bioabsorbable suture anchor with an internal drive head at the proximal end of the suture anchor, and having an insert-molded suture loop that is recessed within the proximal end of the suture anchor.

The insert-molded suture preferably extends through more than half the length of the fully-threaded central body and forms a loop inside a drive socket disposed in the proximal end of the fully-threaded central body. The socket is designed to accept a driver having a drive head with a corresponding geometry and size.

Other features and advantages of the present invention will become apparent from the following description of the invention, which refers to the accompanying drawings.

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

Figures 1, 2:
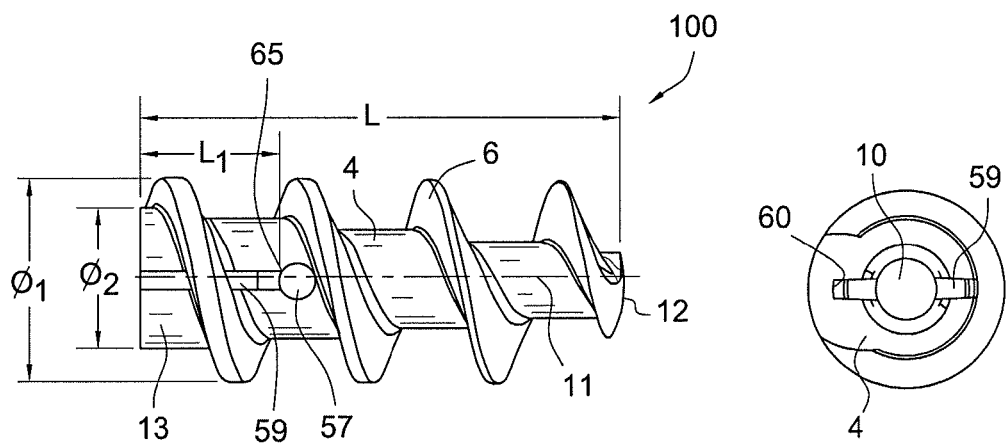
FIG. 1 is a top view of a fully-threaded suture anchor with insert-molded suture according to the present invention.
FIG. 2 is a proximal end view of the fully-threaded suture anchor with insert-molded suture of FIG. 1.
Figure 3:
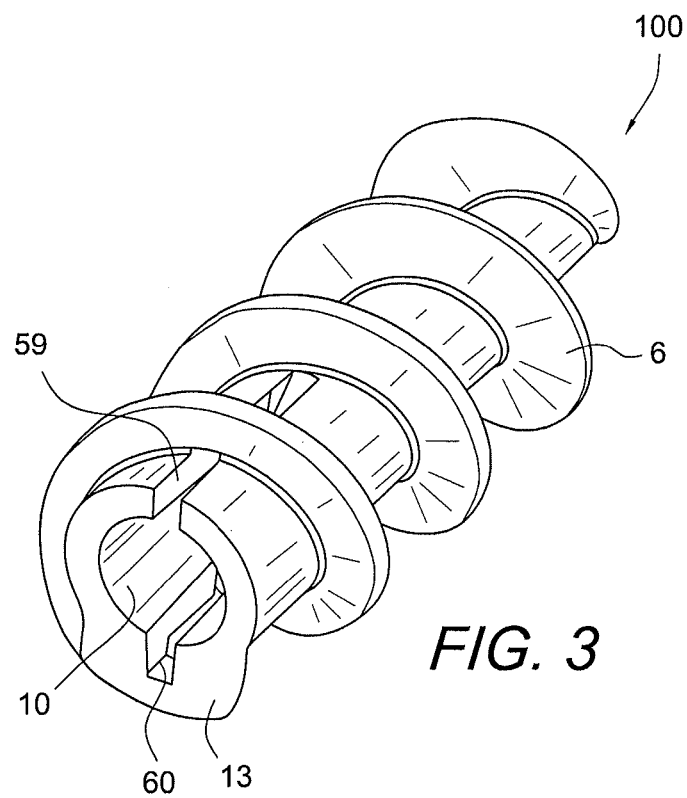
FIG. 3 is a perspective view of the fully-threaded suture anchor with insert-molded suture of FIG. 1.
Figure 4:
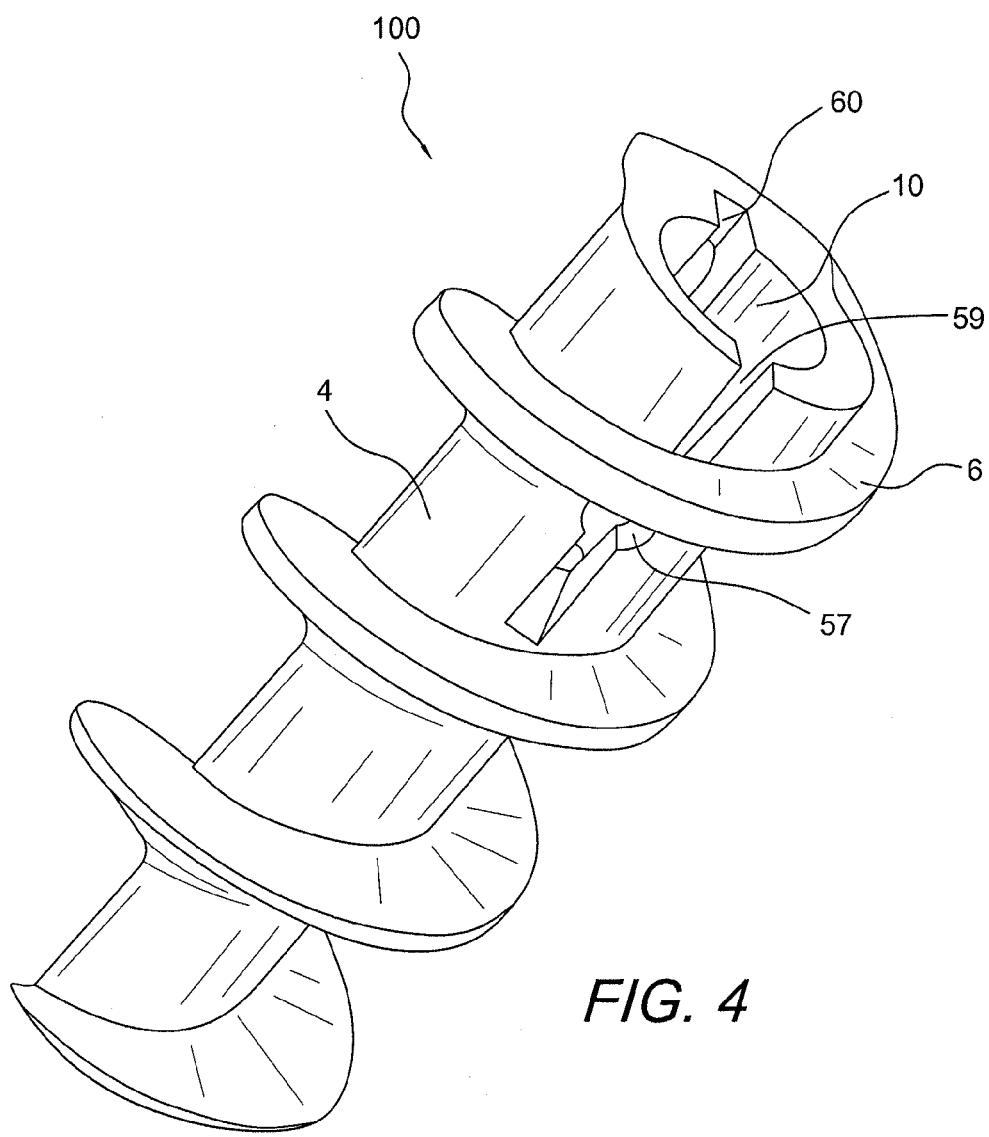
FIG. 4 is another perspective view of the fully-threaded suture anchor with insert-molded suture of FIG. 1.

Referring now to the drawings, where like elements are designated by like reference numerals, FIGS. 1-6 illustrate a fully-threaded bioabsorbable suture anchor 100 of the present invention. The fully-threaded suture anchor 100 includes a body 4 provided in the shape of a tapered cylinder and having a distal end 12 and a proximal end 13. The fully-threaded suture anchor 100 has a tapered inner diameter $\varnothing_2$ and a constant outer diameter $\varnothing_1$. As shown in FIGS. 1, 3 and 4, the fully-threaded suture anchor 100 is provided with a continuous thread 6 which wraps around the body 4 in a clockwise direction, the crest of the threads tapering from wide to narrow from the proximal to the distal end of the anchor. The proximal threads of anchor 100 with the widest crest surfaces are designed to engage the thin cortical shell in osteopenic bone to prevent anchor "pull back," which could cause the back of the anchor to be proud to the bone.

The suture anchor 100 is provided with a drive socket 10 (FIGS. 1-4) in the shape of a tapered cylinder. Transverse holes 57, 58 (FIGS. 1, 3 and 4) for suture loop formation during molding are provided at distal end 65 of the drive socket 10. Socket 10 includes a pair of slots 59, 60 which mate with corresponding protrusions on a driver, as described in greater detail below. Slots 59, 60 extend from the proximal end 13 of the anchor to holes 57, 58.

Figure 5:
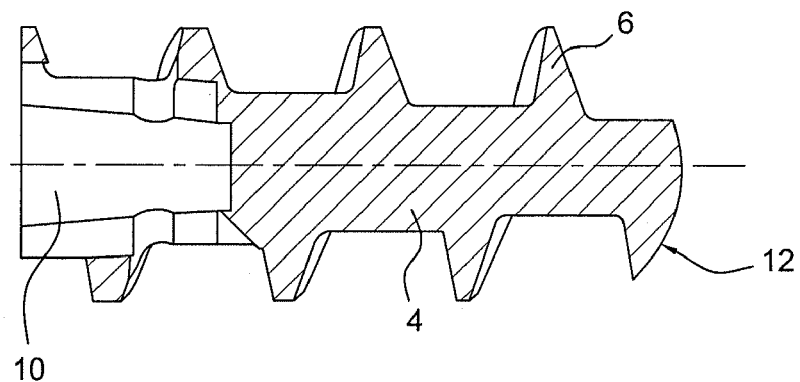
FIG. 5 is a cross-sectional view of the fully-threaded suture anchor of FIG. 1 without insert-molded suture.
Figure 6:
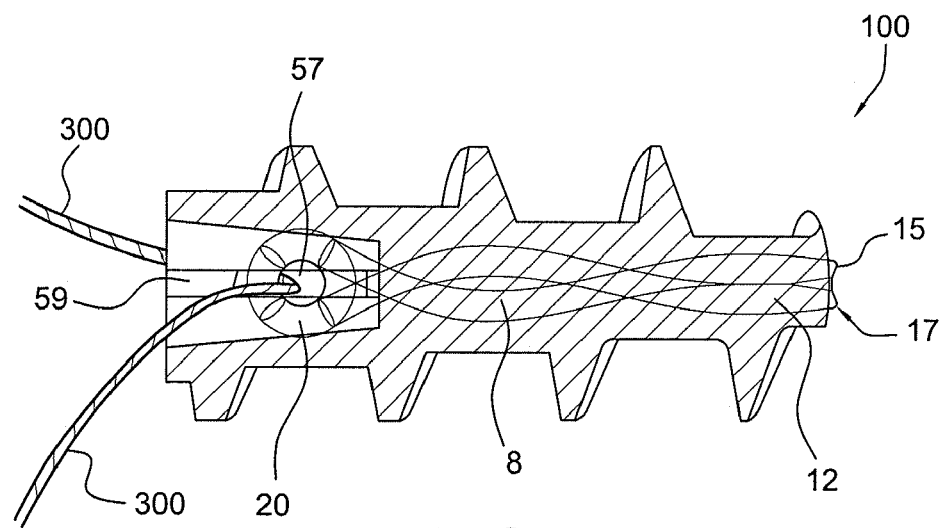
FIG. 6 is a cross-sectional view of the fully-threaded suture anchor of FIG. 1 with insert-molded suture.
Figure 7:
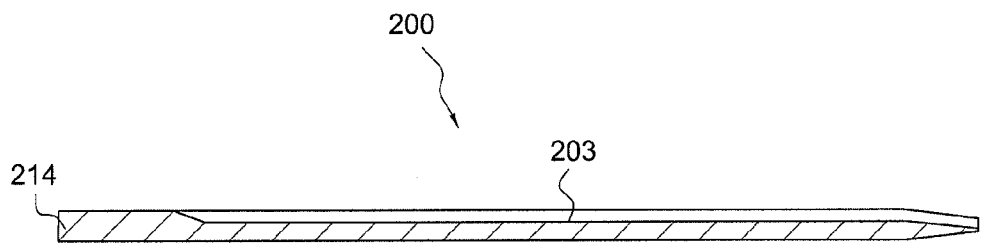
FIG. 7 is a top view of a driver for the fully-threaded suture anchor with insert-molded suture of FIGS. 1-6 according to the present invention.
Figure 8:
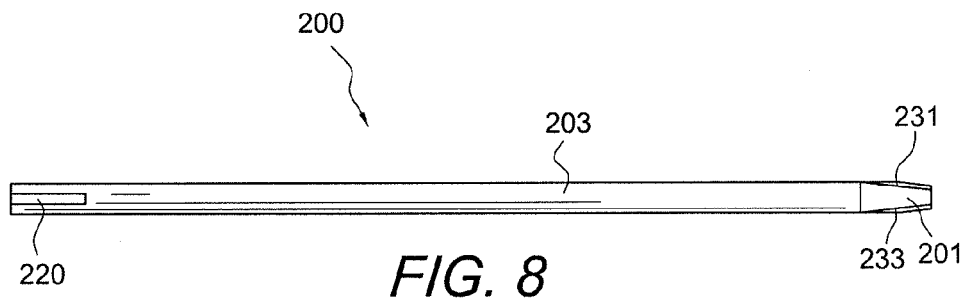
FIG. 8 is another top view of the driver for the fully-threaded suture anchor with insert-molded suture of FIGS. 1-6 according to the present invention.
Figure 9:
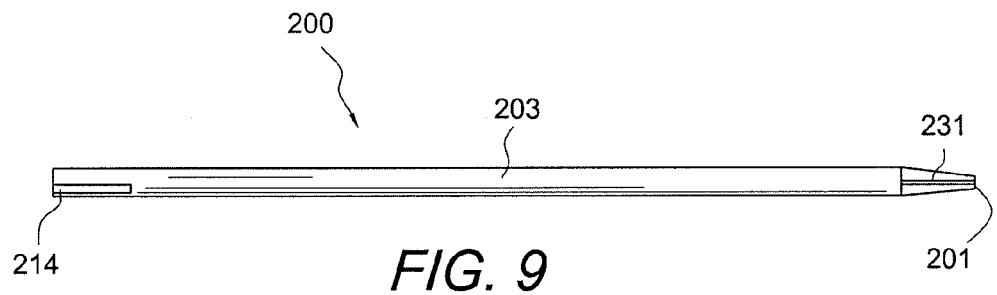
FIG. 9 is a top view of the driver of FIG. 8 rotated ninety degrees.
Figure 10:
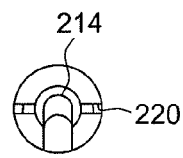
FIG. 10 is an enlarged proximal end view of the driver of FIG. 8.
Figure 11:
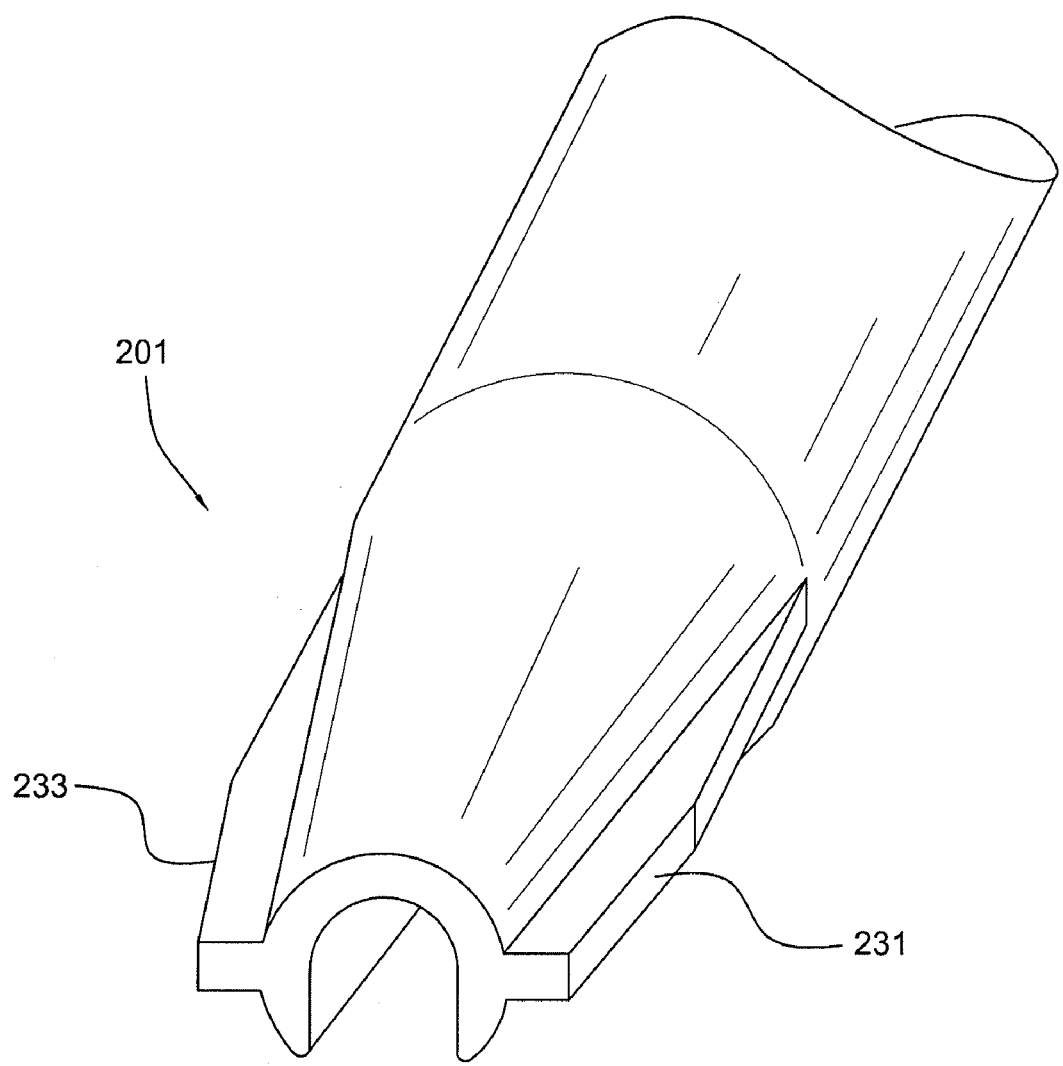
FIG. 11 is an enlarged perspective view of the distal end of the driver of FIG. 8.

Referring now to FIGS. 5 and 6, a strand of suture 8, molded into the anchor body 4 during manufacture, extends through the anchor from the distal end 12 of the suture anchor. Suture 8 is molded inside the suture body 4 in the intertwined shape illustrated in FIG. 6, to increase the pullout strength of the suture from the anchor body. The suture forms a loop or eyelet 20 located within drive socket 10 at the proximal end 13 of the anchor 100 near the suture hole 57. The loop 20 is recessed from the proximal end 13 of the anchor body 4 by a distance $L_1$ (FIG. 1) of about one-third the length L of the anchor body 4. The distance $L_1$ is greater than about half the length L, more preferably about two-thirds the length L. The large, flexible suture eyelet eliminates the need to precisely orientate the eyelet during anchor insertion to optimize suture sliding characteristics.

At the distal end 12 of anchor 100, intertwined suture 8 is preferably trimmed flush to provide a blunt tip 15. Alternatively, a knot can be formed in suture 8 at the distal end of the anchor to increase the pull out strength of the suture from the anchor. The suture 8 is insert-molded into the anchor in the manner described in U.S. Pat. No. 5,964,783 to Grafton et al., noted above.

The anchor body 4 is preferably formed of a translucent or transparent polymer material, and is preferably made of bioabsorbable materials such as polyglycolic or polylactic acid polymers. Accordingly, suture 8 is visible through the body of the fully-threaded anchor 100 to provide visual confirmation of suture encapsulation within the anchor. Advantageously, the suture 8 and the anchor body 4 are made of materials selected such that the suture loop 20 will not biodegrade before anchor body 4.

FIGS. 7-11 illustrate an exemplary embodiment of a cannulated driver 200 used to install the fully-threaded suture anchor 100 of the present invention. As illustrated in FIGS. 7-11, the driver 200 is cannulated on the side and has a head 201 and a shaft 203, the head 201 of the driver being configured to be received within anchor socket 10 of the fully-threaded suture anchor 100 of FIGS. 1-6. Protuberances 231, 233 (FIGS. 8, 9 and 11) are provided on the driver head 201 to engage the slots 59, 60 of anchor socket 10. The anchor 100 and driver 200 are provided to the surgeon as a preformed assembly with a second (knot tying) suture 300 pre-threaded through loop 20 (FIG. 6) and extending through the side cannulation of the driver. The side cannulation (shown as a cannulation on the bottom in FIG. 11) allows the second (knot-tying) suture 300 (which is received in the cannulation) to be provided with large needles on the end, which would not be possible if the driver had a central (fully closed) cannulation.

Suture anchors according to the present invention can be used for arthroscopic procedures. The anchors also are advantageous for open and mini-open surgical procedures. Specific examples of applicable procedures include cortical bone-soft tissue fixation, Bankart and SLAP shoulder repairs. The fully-threaded suture anchor 100 can be made in various sizes, such as a outer diameter of 7.2 mm and an inner diameter which varies between 1.9 mm at the distal end and 4.8 mm at the proximal end, the inner diameter tapering in stepped fashion from the proximal end to the distal end.

A surgical method employing a fully-threaded suture anchor, such as the fully-threaded suture anchor 100 of FIGS. 1-6, generally includes pre-forming a hole for insertion of the anchor using a punch and a tap. The anchor is then engaged with a cannulated driver, such as driver 200 of FIGS. 7-11, inserted into the pilot hole and turned to advance the suture anchor into the bone. The driver is then removed, and the second suture 300 extending through the internal suture loop 20 can then be manipulated and tied to secure soft tissue to bone.

Advantageously, when the fully-threaded suture anchor is inserted into bone, it is not necessary for the proximal end of the anchor to be countersunk below the bone surface, as is required with prior art devices to prevent tissue abrasion by the exposed eyelet. Consequently, the anchor of the present invention does not need to be inserted as far as the prior art devices. Further, the internally disposed suture eyelet avoids abrasion of the rim of bone. In addition, because the fully-threaded suture anchor of the present invention is provided with a fully externally threaded body, better fixation in bone is achieved. Finally, the intertwined suture in the present invention provides greater pull-out strength than prior suture anchors.

Although the present invention has been described in relation to particular embodiments thereof, many other variations and modifications and other uses will become apparent to those skilled in the art.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A suture anchor, comprising:
   a bioabsorbable anchor body having a proximal end and a distal end;
   a suture eyelet formed of a strand of a first suture insert-molded into the bioabsorbable anchor body, the suture eyelet being disposed completely within the anchor body, the first insert-molded suture having an intertwined shape to increase the pullout strength of the suture from the anchor body, and
   a second suture threaded through the suture eyelet and passing slidingly through the eyelet, for tying tissue to bone.

2. The suture anchor of claim 1, wherein the suture anchor has a predetermined length and wherein the suture eyelet is recessed from the proximal end of the anchor body by about one third of the predetermined length.

3. The suture anchor of claim 1, wherein the anchor body is provided with a drive socket at the proximal end, and the suture eyelet is disposed within the drive socket.

4. The suture anchor of claim 3, wherein the drive socket has at least one slot for receiving a corresponding protrusion on a driver head for driving the suture anchor.

5. The suture anchor of claim 1, wherein the anchor body is threaded from the proximal end to the distal end.

6. The suture anchor of claim 1, wherein the anchor body has a a tapered inner diameter.

7. The suture anchor of claim 6, where the taper of the inner diameter is a stepped taper.

8. A suture anchor, comprising:
   a bioabsorbable anchor body having a proximal end, a distal end, and a drive socket at the proximal end;
   a suture eyelet formed of a strand of a first suture insert-molded into the bioabsorbable anchor body, the suture eyelet being disposed completely within the anchor body, the first insert-molded suture having an intertwined shape to increase the pullout strength of the suture from the anchor body, wherein the drive socket has at least one slot for receiving a corresponding protrusion on a driver head for driving the suture anchor and wherein the slot terminates distally in a suture hole provided within the anchor body, and a second suture threaded through the suture eyelet and passing slidingly through the eyelet, for tying tissue to bone.

9. The suture anchor of claim 8, wherein the suture eyelet is transverse to a longitudinal axis of the anchor body.

10. An insert-molded suture anchor, comprising:
a bioabsorbable anchor body having a longitudinal axis, a proximal end and a distal end, the anchor body being threaded between the proximal end and the distal end;
a drive socket provided at the proximal end;
a suture loop disposed completely within the drive socket of the anchor body, the suture loop being formed of a strand of suture insert-molded into the anchor body, the insert-molded suture having an intertwined shape to increase the pullout strength of the suture from the anchor body, and a second suture threaded through the suture loop and passing slidingly through the suture loop, for tying tissue to bone.

11. The insert-molded suture anchor of claim 10, wherein the suture loop is recessed from the proximal end of the anchor body by about one third the length of the anchor body.

12. The insert-molded suture anchor of claim 10, wherein the drive socket has at least one slot for receiving a correspondingly shaped protrusion on a driver.

13. The insert-molded suture anchor of claim 10, wherein the anchor thread extending between the proximal end and the distal end of the body has a crest which tapers from wide to narrow from the proximal end to the distal end of the body.

14. The insert-molded suture anchor of claim 12, wherein the anchor body is threaded.

15. The insert-molded suture anchor of claim 10, wherein the threaded anchor body has a tapered inner diameter.

16. The insert-molded suture anchor of claim 15, wherein the taper of the inner diameter is a stepped taper.

17. The insert-molded suture anchor of claim 10, wherein the suture loop is a suture eyelet.

* * * * *